United States Patent [19]

Cohen

[11] 4,403,609
[45] Sep. 13, 1983

[54] VACUUM-COMPRESSION INJECTOR

[76] Inventor: Edgar C. Cohen, 4123 Vincennes Place, New Orleans, La. 70125

[21] Appl. No.: 237,563

[22] Filed: Feb. 24, 1981

[51] Int. Cl.³ .............................................. A61M 5/30
[52] U.S. Cl. ...................................... 604/70; 604/245
[58] Field of Search ...................... 128/207.23, 207.24, 128/207.25, 215 R, 218 R, 218 F, DIG. 1

[56] References Cited

U.S. PATENT DOCUMENTS

| | | | |
|---|---|---|---|
| 1,934,046 | 11/1933 | Demarchi | 128/215 |
| 2,743,723 | 5/1956 | Hein | 128/215 |
| 2,945,496 | 7/1960 | Fosdal | 128/215 |
| 3,057,349 | 10/1962 | Ismach | 128/207.23 |
| 3,140,713 | 7/1964 | Ismach | 128/207.23 |
| 3,167,071 | 1/1965 | Venditty | 128/207.25 |
| 3,424,154 | 1/1969 | Kinsley | 128/207.25 |
| 3,490,451 | 1/1970 | Yahner | 128/207.23 |
| 3,515,130 | 6/1970 | Tsujino | 128/207.25 |
| 3,548,830 | 12/1970 | Goey | 128/361 |
| 3,688,765 | 9/1972 | Gasaway | 128/207.25 |
| 3,933,155 | 1/1976 | Johnston | 128/207.23 |
| 4,284,077 | 8/1981 | Wagner | 128/215 |

Primary Examiner—Henry J. Recla
Attorney, Agent, or Firm—Griffin, Branigan & Butler

[57] ABSTRACT

A needless vacuum-compression injector stabilizes a nozzle over the tissue to be penetrated by means of a continuous vacuum applied to an annular area surrounding the point of penetration. The vacuum draws the tissue toward the annular region and immobilizes the tissue over the nozzle without puncturing the tissue and without substantially displacing the tissue from its initial condition. Pressurized gas is used to express a medicament through an orifice in the nozzle and into the immobilized tissue.

10 Claims, 3 Drawing Figures

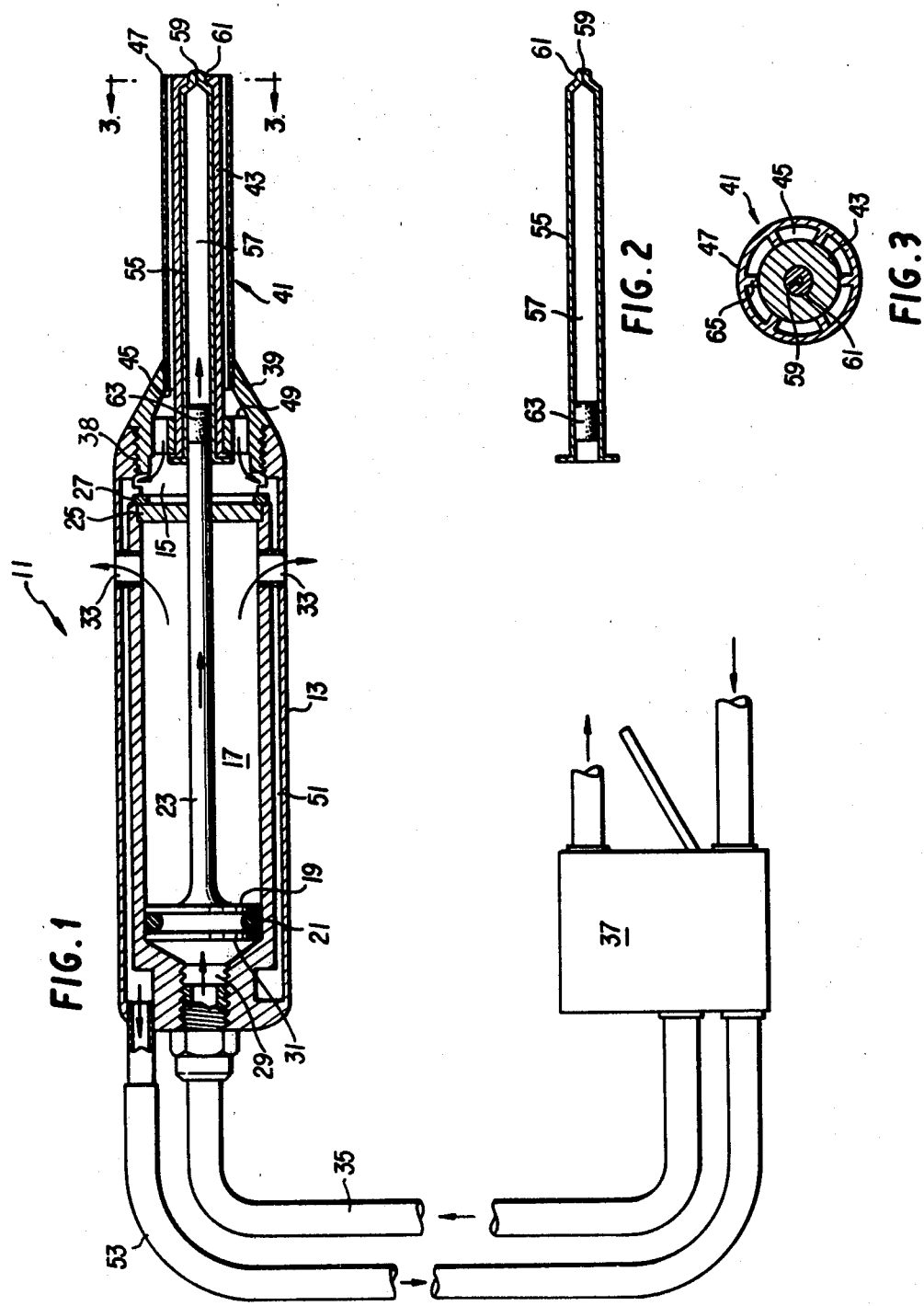

4,403,609

VACUUM-COMPRESSION INJECTOR

This invention is in the field of hypodermic and hypomucosal injectors using pressurized air to force a medicament into the tissue.

BACKGROUND

The concept of using pressurized air to inject a fluid through the skin of a human being or an animal is not new. U.S. Pat. No. 3,140,713 to Ismach, for example, discloses a conventional jet injection device with an intradermal nozzle designed to inject fluid at an angle of 45° to control the depth of penetration and prevent tearing or rupturing of the skin. In this regard, it has been found that the pressure entry of liquid into non-fixed, movable soft tissue at various angles creates undesirable tearing, hemorrhage and subsequent post-operative pain. As a result, the use of existing jet injectors have not overcome the physical and psychological traumatic effects of a syringe and needle—particularly in the field of oral injections into mucosa.

SUMMARY

The present invention overcomes the above objections to jet hypodermic injector devices by using a vacuum to stabilize a nozzle of the device over the tissue to be penetrated. In this respect, the suction pulls the tissue taut and draws it over an orifice of the nozzle so that the nozzle and tissue are essentially immobile relative to each other. This then eliminates the entry of medicament liquids at various angles; eliminates the resultant tearing of the soft tissue; and, reduces the accompanying pain. The structure of the invention also includes an air driven piston which provides for a smooth delivery of the medicament into the tissue and precludes the undesirable shock wave that is generated in the soft tissue by prior art spring-driven-piston devices.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout different views. The drawings are not necessarily to scale, emphasis instead being placed upon illustrating principles of the invention.

FIG. 1 is a partial cross-sectional view of a vacuum compression injector according to principles of this invention;

FIG. 2 is a schematic partial cross-sectional view of a medicament insert; and,

FIG. 3 is a cross-sectional view of an embodiment of the invention taken along lines 3—3 of FIG. 1.

DESCRIPTION OF PREFERRED EMBODIMENTS

A vacuum-compression injector 11 of the invention is illustrated in FIG. 1. Therein, an exterior cylindrical housing 13 contains a vacuum chamber 15 and an interior cylindrical chamber 17. The interior cylindrical chamber 17 contains a movable piston 19 with an o-ring 21 providing an air-tight seal between the piston 19 and the interior of cylindrical chamber 17. The piston 19 has a piston rod or plunger 23 extending forwardly in the interior chamber 17 and maintained in an axial position by a guide bushing 25 which is held in position by a retaining ring 27 at the right end of the interior chamber 17 in FIG. 1.

The other end of the interior cylindrical chamber 17 contains a port 29 through which air under pressure enters and impinges upon a face 31 of the piston 19.

The right end of the interior cylindrical chamber 17 adjacent to the piston rod guide bushing 25 has a plurality of vents 33 opening through the cylindrical housing 13 to the atmosphere.

The air supply port 29 is connected by an air supply line 35 to a two-phase pneumatic switch 37 which, in turn, is connected to an air supply source (not shown).

The right end of the cylindrical housing 13 in FIG. 1 has interior threads 38 for threadably joining the tapered base 39 of a generally cylindrical nozzle housing 41. The cylindrical nozzle housing 41 contains a hollow concentric cylindrical medicament-insert-holder 43 which is spaced from the interior of the cylindrical housing 41 leaving an annular passageway 45 extending from a forward end 47 of housing 41 back through a plurality of vacuum ports 49 to the vacuum chamber 15. The vacuum chamber 15 is connected to a second annular passageway 51 contained within the cylindrical housing 13. This second passageway 51 extends to the end of the housing 13 where it joins a vacuum line 53. The vacuum line 53 is connected through the two phase pneumatic switch 37 to a source of vacuum (not shown).

A cylindrical medicament insert 55 (FIG. 2) has an interior cavity 57 for storing a supply of medicament. The medicament insert 55 has an orifice 59 at its forward end 61 and is sealed at its other end by a plunger-plug 63.

As can be seen in FIG. 3, the forward end 47 of the housing 41 is spaced from the medicament insert holder 43 by a plurality of spacers 65 defining the annular vacuum passageway 45. The forward end 61 of the medicament insert 55 protrudes through the forward end wall of the insert holder 43, as shown in FIGS. 1 and 3.

The medicament orifice 59 in the insert 55 is centrally located in the forward end 61 of the insert 55 to form a nozzle as can be seen in FIGS. 2 and 3. In an alternative embodiment, not shown, the nozzle is formed integrally with the housing 43 and the insert 55 located therebehind but; of course, in communication with the passageway leading to orifice 59. In still another alternative embodiment, the insert is essentially stationary with medicament being supplied thereto from an outside source as required.

In operation, with a medicament insert 55 in position within the holder 43 of the housing 41, the two phase pneumatic switch 37 is initially depressed halfway to open the vacuum source through line 53 and intervening passageway 51, chamber 15, and passageway 45 to the forward end 47 of the housing 41 to draw a patient's tissue firmly over the forward end 61 of the medicament insert 55 and its orifice 59. In this manner the tissue is immobilized. The two phase pneumatic switch 37 is then fully depressed to release a charge of compressed air through line 35 to impinge upon the piston face 31 driving the piston 19 forward in the interior chamber 17. At the same time the piston rod 23 drives the plunger-plug 63 forward in the medicament insert 55 forcing the medicament out through the passageway leading to orifice 59 (and orifice 59 itself) with sufficient force to penetrate the soft tissue of the patient. As this occurs air trapped forward of the piston 19 is exhausted from the chamber 17 through the vents 33 to the atmosphere.

After the injection has been completed, the nozzle 41 is unscrewed from the cylindrical housing 13 and the cylindrical medicament insert 55 is removed from the insert holder 43 and disposed of. A new medicament insert 55 containing a medicament charge is then inserted into the holder 43. Pressure is then exerted against the piston rod 23 to return the piston 19 to its aft position in the cylindrical housing 13 and then the housing 41 is again threaded into the cylindrical housing 13.

As has been illustrated, the patient's tissue is immobilized by using an annular ring of vacuum to draw the patient's tissue tightly over the orifice of a pressure injector prior to discharging it through the dermis or mucosa so as to prevent the trauma of tearing the tissue and the related post-operative pain.

In addition, the replaceable medicament insert 55 with its forward end 61 and orifice 59 provide a completely sanitary and safe means for using the injector on a series of patients or for interchanging the medicaments between injections.

While the invention has been particularly shown and described with reference to preferred embodiments thereof, it will be understood by those skilled in the art that various alterations in form and detail may be made therein without departing from the spirit and scope of the invention.

The embodiments of the invention in which an exclusive property or privilege is claimed are defined as follows:

1. A needleless vacuum-compression injector comprising:
   a continuous vacuum chamber and a pressurized gas chamber;
   means for drawing a continuous vacuum in said vacuum chamber;
   means for supplying pressurized gas to said pressurized gas chamber;
   means for holding a medicament;
   a nozzle having a passageway connected to said means for holding said medicament and for having said medicament expressed therethrough;
   tissue immobilizing means including an outwardly extending surface spaced from and surrounding said nozzle wherein said nozzle substantially terminates in the plane of said surface;
   said tissue immobilizing means further including an annular suction means formed in an annular region of said outwardly extending surface and spaced from and surrounding said nozzle, said annular suction means being in continuous communication with said vacuum chamber, said tissue immobilizing means, when positioned against said tissue, being operative to continuously draw said tissue toward said annular region and thereby immobilize and hold said tissue taut over said nozzle without puncturing said tissue and without substantially displacing said tissue from its initial condition; and,
   means adapted to express said medicament through said passageway and into said tissue upon application of said pressurized gas to said pressurized gas chamber.

2. The apparatus of claim 1 including control means for selectively connecting said means for drawing said vacuum and said means for supplying said pressurized gas to said vacuum chamber and said pressurized gas chamber respectively.

3. The apparatus of claim 1 wherein said means to express said medicament through said nozzle and into said tissue includes a piston having one end thereof closing said pressurized air chamber and the other end thereof engaging said means for holding said medicament and adapted so that motion of said piston toward said engaging end expresses said medicament through said nozzle and into said tissue.

4. The apparatus of claim 1 wherein said means for holding said medicament is selectively insertable into said injector.

5. The apparatus of claim 1 wherein said means for holding said medicament includes a moveable plug at one end thereof.

6. The apparatus of claim 5 wherein said means to express said medicament through said nozzle and into said tissue includes a piston having one end thereof closing said pressurized gas chamber and the other end thereof engaging said plug so that motion of said piston toward said engaging end expresses said medicament through said nozzle and into said tissue.

7. The apparatus of claim 1 further comprising:
   a housing containing said vacuum chamber and said pressurized air chamber and including:
   a piston slidably located within a piston chamber in said housing and having a first end thereof exposed to said pressurized air chamber;
   a plunger affixed at one end to the other end of said piston so as to be slidably movable with said piston and engageable at its other end with said means for holding medicament so that motion of said piston causes said medicament to be expressed through said nozzle and into said tissue.

8. The apparatus of claim 7 including a bushing in said housing for slidably supporting the other end of said plunger.

9. The apparatus according to claim 7 including vent holes in said housing and in communication with said piston chamber on the other side of said piston so that air is permitted to vent out of said vents during motion of said piston as said medicament is expressed.

10. A needleless method for injecting a medicament through a nozzle and into the tissue of a patient comprising the steps of:
   immobilizing a selected portion of said tissue by continuously applying a vacuum to said tissue in an annular area spaced from the location on said tissue where said medicament is to be injected; and,
   drawing said selected portion of said tissue over said nozzle and continuously holding said tissue taut without puncturing said tissue and without substantially displacing said tissue from its initial condition; and,
   injecting said medicament into said tissue at said location where said tissue is tautly immobilized by the continuous suction applied to said annular area.

* * * * *